United States Patent [19]

Lautenschläger et al.

[11] Patent Number: 4,552,869
[45] Date of Patent: Nov. 12, 1985

[54] O-ALKYL-O-CARBAMOYLGLYCEROPHOSPHOCHOLINES AND THE USE FOR TREATING HYPERTENSION

[75] Inventors: Hans-Heiner Lautenschläger, Pulheim-Stommeln; Hans Betzing, Kerpen-Horrem; Gerrit Prop, Pulheim; Ottfried Zierenberg, Cologne, all of Fed. Rep. of Germany

[73] Assignee: A. Nattermann & Cie GmbH, Cologne, Fed. Rep. of Germany

[21] Appl. No.: 621,131

[22] Filed: Jun. 15, 1984

Related U.S. Application Data

[63] Continuation of Ser. No. 404,716, Aug. 3, 1982, abandoned.

[30] Foreign Application Priority Data

Aug. 12, 1981 [DE] Fed. Rep. of Germany ....... 3131782
Aug. 12, 1981 [DE] Fed. Rep. of Germany ....... 3131783
Dec. 24, 1981 [DE] Fed. Rep. of Germany ....... 3151377
Dec. 24, 1981 [DE] Fed. Rep. of Germany ....... 3151378

[51] Int. Cl.$^4$ .................... A61K 31/685; C07F 9/10
[52] U.S. Cl. ........................................ 514/77; 260/925
[58] Field of Search ........................... 260/925; 514/77

[56] References Cited

FOREIGN PATENT DOCUMENTS

| 0035375 | 9/1981 | European Pat. Off. ............ 424/199 |
| 0094186 | 11/1983 | European Pat. Off. ............ 260/925 |
| 0002636 | 1/1980 | Japan ................................... 424/199 |
| 1523965 | 9/1978 | United Kingdom . |

OTHER PUBLICATIONS

Breithaput, "Med. Welt," vol. 33, (1982), p. 1141 A.
Buchborn et al., "Therapy of Internal Diseases," (1973), p. 5, B.
H. A. Staab and Dr. W. Rohr: Synthesen mit Heterocyclischen Amiden (Azoliden), p. 79, Weinheim, 1967.
Blank et al.: Biochemical and Biophysical Research Communications 90 (4), p. 1194 et seq., (1979).
Muramatsu et al.: Chemistry and Physics of Lipids, 29, (1981), pp. 121–127.
Zeidler: Fette-Seifen-Anstrichmittel 83 (2) 57, (1981).
Mangold: Angew. Chemie 91, 550–560, (1979).

*Primary Examiner*—Anton H. Sutto
*Attorney, Agent, or Firm*—Pearne, Gordon, Sessions, McCoy, Granger & Tilberry

[57] ABSTRACT

The present invention relates to new O-alkyl-O-carbamoylglycerophosphocholines of the general formulae I or II

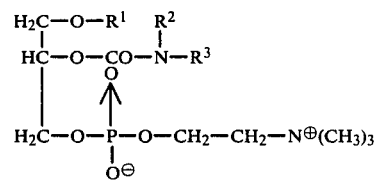

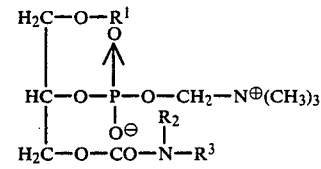

and processes for treating human beings suffering from diseases caused by hypertension by administering one or several of the above compounds.

11 Claims, No Drawings

O-ALKYL-O-CARBAMOYLGLYCEROPHOSPHO-CHOLINES AND THE USE FOR TREATING HYPERTENSION

This is a continuation of application Ser. No. 404,716, filed on Aug. 3, 1982, now abandoned.

The present invention relates to new O-alkyl-O-carbamoylglycerophosphocholines and their use in the treatment of human beings suffering from diseases caused by hypertension.

The compounds according to the invention correspond to the general formulae I or II

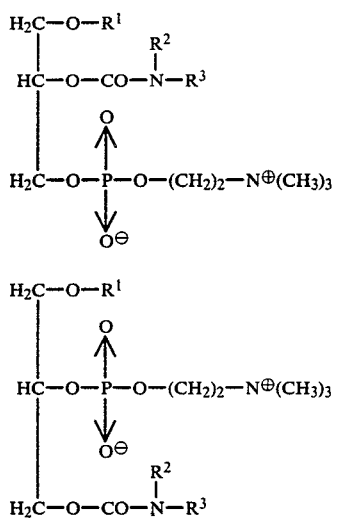

wherein $R^1$ denotes a straight-chain, saturated or unsaturated hydrocarbon radical having 10–20 C atoms, while $R^2$ and $R^3$ can be identical or different and denote a straight-chain or branched, saturated or unsaturated hydrocarbon radical having 1–20 C atoms, or a hydrogen atom.

The following are examples of compounds according to the invention:

1-O-hexadecyl-2-O-methylcarbamoylglycero-3-phosphocholine,
2-O-ethylcarbamoyl-1-O-hexadecylglycero-3-phosphocholine,
1-O-hexadecyl-2-O-propylcarbamoylglycero-3-phosphocholine,
1-O-hexadecyl-2-O-isopropylcarbamoylglycero-3-phosphocholine,
2-O-butylcarbamoyl-1-O-hexadecylglycero-3-phosphocholine,
1-O-hexadecyl-2-O-pentylcarbamoylglycero-3-phosphocholine,
1-O-hexadecyl-2-O-hexylcarbamoylglycero-3-phosphocholine,
2-O-methylcarbamoyl-1-O-octadecylglycero-3-phosphocholine,
2-O-ethylcarbamoyl-1-O-octadecylglycero-3-phosphocholine,
1-O-octadecyl-2-O-propylcarbamoylglycero-3-phosphocholine,
2-O-isopropylcarbamoyl-1-O-octadecylglycero-3-phosphocholine,
2-O-butylcarbamoyl-1-O-octadecylglycero-3-phosphocholine,
1-O-octadecyl-2-O-pentylcarbamoylglycero-3-phosphocholine,
2-O-hexylcarbamoyl-1-O-octadecylglycero-3-phosphocholine,
1-O-hexadecyl-3-O-methylcarbamoylglycero-2-phosphocholine,
3-O-ethylcarbamoyl-1-O-hexadecylglycero-2-phosphocholine,
1-O-hexadecyl-3-O-propylcarbamoylglycero-2-phosphocholine,
1-O-hexadecyl-3-O-isopropylcarbamoylglycero-2-phosphocholine,
3-O-butylcarbamoyl-1-O-hexadecylglycero-2-phosphocholine,
1-O-hexadecyl-3-O-pentylcarbamoylglycero-2-phosphocholine,
1-O-hexadecyl-3-O-hexylcarbamoylglycero-2-phosphocholine,
3-O-methylcarbamoyl-1-O-octadecylglycero-2-phosphocholine,
3-O-ethylcarbamoyl-1-O-octadecylglycero-2-phosphocholine,
1-O-octadecyl-3-O-propylcarbamoylglycero-2-phosphocholine,
3-O-isopropylcarbamoyl-1-O-octadecylglycero-2-phosphocholine,
3-O-butylcarbamoyl-1-O-octadecylglycero-2-phosphocholine,
1-O-octadecyl-3-O-pentylcarbamoylglycero-2-phosphocholine,
3-O-hexylcarbamoyl-1-O-octadecylglycero-2-phosphocholine,
3-O-methylcarbamoyl-1-O-oleylglycero-2-phosphocholine,
3-O-ethylcarbamoyl-1-O-linolylglycero-2-phosphocholine,
3-O-dimethylcarbamoyl-1-O-octadecylglycero-2-phosphocholine,
3-O-dimethylcarbamoyl-1-O-hexadecylglycero-2-phosphocholine,
2-O-decylcarbamoyl-1-O-hexadecylglycero-3-phosphocholine,
1-O-hexadecyl-2-O-undecylcarbamoylglycero-3-phosphocholine,
2-O-dodecylcarbamoyl-1-O-hexadecylglycero-3-phosphocholine,
1-O-hexadecyl-2-O-tetradecylcarbamoylglycero-3-phosphocholine,
1-O-hexadecyl-2-O-hexadecylcarbamoylglycero-3-phosphocholine,
1-O-hexadecyl-2-O-octadecylcarbamoylglycero-3-phosphocholine,
2-O-eicosylcarbamoyl-1-O-hexadecylglycero-3-phosphocholine,
2-O-decylcarbamoyl-1-O-octadecylglycero-3-phosphocholine,
1-O-octadecyl-2-O-undecylcarbamoylglycero-3-phosphocholine,
2-O-dodecylcarbamoyl-1-O-octadecylglycero-3-phosphocholine,
1-O-octadecyl-2-O-tetradecylcarbamoylglycero-3-phosphocholine,
2-O-hexadecylcarbamoyl-1-O-octadecylglycero-3-phosphocholine,
1-O-octadecyl-2-O-octadecylcarbamoylglycero-3-phosphocholine,
2-O-eicosylcarbamoyl-1-O-octadecylglycero-3-phosphocholine, 3-O-decylcarbamoyl-1-O-hexadecylglycero-2-phosphocholine,
1-O-hexadecyl-3-O-undecylcarbamoylglycero-2-phosphocholine,
3-O-dodecylcarbamoyl-1-O-hexadecylglycero-2-phosphocholine,
1-O-hexadecyl-3-O-tetradecylcarbamoylglycero-2-phosphocholine, contrast to these phospholipids, they are stable to phospholipase $A_2$ and thus make possible a better transmission of the included active compound to the site of action.

The substances according to the invention are prepared by reacting the lyso compounds III or IV wherein $R^1$ has the meaning mentioned in claim 1, with the appropriate alkyl isocyanates of the formula VI

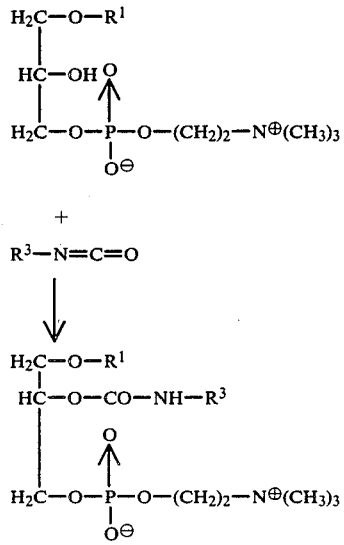

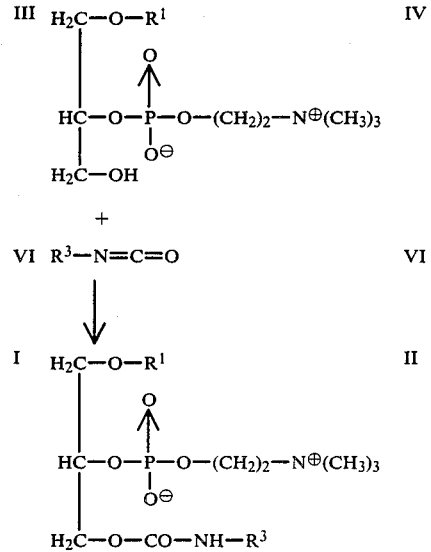

1-O-hexadecyl-3-O-hexadecylcarbamoylglycero-2-phosphocholine,
1-O-hexadecyl-3-O-octadecylcarbamoylglycero-2-phosphocholine,
3-O-hexadecylcarbamoyl-1-O-oleylglycero-2-phosphocholine,
3-O-hexadecylcarbamoyl-1-O-linolylglycero-2-phosphocholine,
3-O-hexadecylcarbamoyl-1-O-octadecylglycero-2-phosphocholine,
1-O-octadecyl- -O-octadecylcarbamoylglycero-2-phosphocholine and
3-O-eicosylcarbamoyl-1-O-octadecylglycero-2-phosphocholine.

The compounds according to the invention have valuable pharmacological properties, i.e. antihypertensive properties, antirheumatic properties or antiartherosclerotic properties and are therefore suitable for use as an active compound in medicaments for human beings in dosages usual for antihypertensive agents.

Amongst the compounds according to the invention which have been listed, substances such as, for example, 1-O-hexadecyl-2-O-methylcarbamoylglycero-3-phosphocholine or 2-O-ethylcarbamoyl-1-O-hexadecylglycero-3-phosphocholine are particularly preferred, because they exhibit a very strong antihypertensive action and also an advantageous effect against rheumatic diseases. The said compounds can, therefore, be used for treating hypertension and various rheumatic, and a few atherosclerotic, clinical pictures in humans.

In addition, compounds such as, for example, 1-O-hexadecyl-2-O-hexadecylcarbamoylglycero-3-phosphocholine or 1-O-hexadecyl-3-O-hexadecylcarbamoylglycero-2-phosphocholine are preferred, since they possess distinct advantages compared with the natural or synthetic 1,2-diacylglycero-3-phosphocholines hitherto used in liposome techniques, since, in The reaction is advantageously carried out in organic aprotic solvents, such as, for example, chloroform, acetone or dimethylformamide or mixtures thereof, if appropriate using a catalyst, in particular a Lewis base, such as, for example, triethylamine, pyridine, dimethylaminopyridine or dimethylformamide, at temperatures between 0° and 100° C., preferably at 40°–60° C. The isocyanates can also be employed under the above-mentioned conditions in the form of their imidazolides of the general formula VII

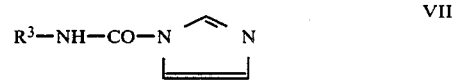

since the imidazolides behave like free isocyanates (compare H. A. Staab and W. Rohr in: Neuere Methoden der präparativen organischen Chemie ("Recent Methods of preparative organic Chemistry"), page 79, Weinheim 1967).

The following are examples of suitable starting compounds III or IV:
1-O-decylglycero-3-phosphocholine,
1-O-undecylglycero-3-phosphocholine,
1-O-dodecylglycero-3-phosphocholine,
1-O-tridecylglycero-3-phosphocholine,
1-O-tetradecylglycero-3-phosphocholine,
1-O-pentadecylglycero-3-phosphocholine,
1-O-hexadecylglycero-3-phosphocholine,
1-O-heptadecylglycero-3-phosphocholine,
1-O-octadecylglycero-3-phosphocholine,
1-O-nonadecylglycero-3-phosphocholine,
1-O-eicosylglycero-3-phosphocholine,
1-O-decylglycero-2-phosphocholine, 1-O-undecylglycero-2-phosphocholine,
1-O-dodecylglycero-2-phosphocholine,
1-O-tridecylglycero-2-phosphocholine,
1-O-tetradecylglycero-2-phosphocholine,
1-O-pentadecylglycero-2-phosphocholine,
1-O-hexadecylglycero-2-phosphocholine,
1-O-heptadecylglycero-2-phosphocholine,
1-O-octadecylglycero-2-phosphocholine,
1-O-oleylglycero-2-phosphocholine,
1-O-linolylglycero-2-phosphocholine,
1-O-nonadecylglycero-2-phosphocholine and
1-O-eicosylglycero-2-phosphocholine,
it being possible to employ the lyso compounds in the natural sn-form, in the form of their mirror image isomers or in the form of racemates.

The following are examples of suitable starting compounds VI: methyl isocyanate, ethyl isocyanate, propyl isocyanate, isopropyl isocyanate, butyl isocyanate, pentyl isocyanate, hexyl isocyanate, decyl isocyanate, undecyl isocyanate, dodecyl isocyanate, tridecyl isocyanate, tetradecyl isocyanate, pentadecyl isocyanate, hexadecyl isocyanate, octadecyl isocyanate, nonadecyl isocyanate and eicosyl isocyanate.

The 1-O-alkyl-3-phosphocholines III which are employed as starting compounds are either accessible by extraction of organs (for example M. Blank et al., Biochemical and Biophysical Research Communications 90 (4), 1194 et seq. (1979)) or can be synthesised by the customary methods, for example by enzymatic cleavage (phospholipase A$_2$) or mild alkaline hydrolysis, from the corresponding 2-O-acyl-1-O-alkylglycero-3-phosphocholines.

The 1-O-alkylglycero-2-phosphocholines IV which are employed as starting compounds can be obtained by mild alkaline hydrolysis from O-acyl-O-alkylglycero-2-phosphocholines, which can be obtained from glycerol derivatives of the formula VIII

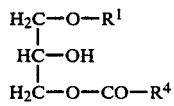

in which R$^1$ has the meaning indicated in claim 1 and R$^4$ denotes a straight-chain or branched hydrocarbon radical having 1-6 C atoms, by known phosphorilation processes, such as, for example, reaction with β-bromoethylphosphoric acid dichloride in the presence of a base and subsequent treatment with trimethylamine (compare, for example, T. Muramatsu et al., Chemistry and Physics of Lipids 29, 121-127 (1981)).

The glycerol derivatives VIII are in turn accessible from 2,3-epoxypropyl ethers by reaction with the appropriate acids R$^4$COOH analogously to the process described for ester-alcohols by U. Zeidler, Fette, Seifen, Anstrichmittel 83 (2), 57 (1981). 2,3-Epoxy ethers are obtained from epichlorohydrins and the corresponding alcohols R$^1$OH, best by phase transfer catalysis in accordance with methods which are known from the literature. On the other hand, glycerol derivatives VIII can also be obtained by isomerisation from the corresponding 2-O-acylglycerol ethers IX

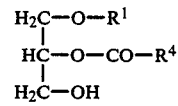

for example simply by warming. The synthesis of the 2-O-acylglycerol ethers is described by K. Mangold, Angew. Chemie 91, 550-560 (1979).

1-O-Alkyl-3-O-dialkylcarbamoylglycero-2-phosphocholine can be prepared from the said lyso compounds IV by reaction with dialkylcarbamoylhalides, in particular with chlorides of the formula V

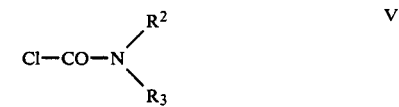

such as, for example, N,N-dimethylcarbamoyl chloride, N-ethyl-N-methylcarbamoyl chloride, N,N-diethylcarbamoyl chloride, N-methyl-N-propylcarbamoyl chloride and N,N-dipropylcarbamoyl chloride, in inert organic solvents, such as, for example, chloroform, and also solvent mixtures, if appropriate with the addition of customary bases, such as, for example, tertiary amines, metal oxides or metal carbonates.

The preparation of the compounds according to the invention is illustrated in greater detail by means of the examples which follow. Since the compounds cannot be characterised by melting points because of their wax-like consistency, the appropriate IR data and Rf values of the substances are quoted. The IR spectra were recorded using the Perkin-Elmer 257 instrument, the substances being subjected to measurement in the form of solutions in chloroform. Thin-layer chromatography: silica gel 60F-254, may be Merck; migrating agent: chloroform/methanol/water=65/25/4 (v/v/v).

EXAMPLE 1

1-O-Hexadecyl-2-O-methylcarbamoylglycero-3-phosphocholine. A mixture of 50 mg of 1-O-hexadecylglycero-3-phosphocholine, 24 mg of methyl isocyanate, 50 ml of absolute chloroform and 0.1 ml of dimethylformamide is stirred at 40°-60° C. until the lysophospholipid can no longer be detected by thin-layer chromatography (Rf: 0.23). The solvent and excess alkyl isocyanate are removed in vacuo and the residue is purified by column chromatography (silica gel: chloroform/methanol/water).

Yield: 41 mg, Rf: 0.26, IR: 1715 cm$^{-1}$.

The following are prepared analogously to these directions:

EXAMPLE 2

2-O-Ethylcarbamoyl-1-O-hexadecylglycero-3-phosphocholine from 50 mg of 1-O-hexadecylglycero-3-phosphocholine and 28 mg of ethyl isocyanate in 5 ml of chloroform and 0.1 ml of dimethylformamide.

Yield: 47 mg, Rf: 0.30, IR: 1710 cm$^{-1}$.

EXAMPLE 3

1-O-Hexadecyl-2-O-propylcarbamoylglycero-3-phosphocholine from 50 mg of 1-O-hexadecylglycero-3-phosphocholine and 34 mg of propyl isocyanate in 5 ml of chloroform and 0.1 ml of dimethylformamide.

Yield: 38 mg, Rf: 0.34, IR: 1715 cm$^{-1}$.

EXAMPLE 4

1-O-Hexadecyl-2-O-isopropylcarbamoylglycero-3-phosphocholine from 50 mg of 1-O-hexadecylglycero-3-phosphocholine and 34 mg of isopropyl isocyanate in 5 ml of chloroform and 0.1 ml of dimethylformamide.

Yield: 35 mg, Rf: 0.35, IR: 1716 cm$^{-1}$.

EXAMPLE 5

2-O-Butylcarbamoyl-1-O-hexadecylglycero-3-phosphocholine from 50 mg of 1-O-hexadecylglycero-3-phosphocholine and 40 mg of butyl isocyanate in 5 ml of chloroform and 0.1 ml of dimethylformamide.

Yield: 40 mg, Rf: 0.37, IR: 1712 cm$^{-1}$.

The following are prepared analogously to Examples 1–5:

1-O-hexadecyl-2-O-pentylcarbamoylglycero-3-phosphocholine,
1-O-hexadecyl-2-O-hexylcarbamoylglycero-3-phosphocholine,
2-O-methylcarbamoyl-1-O-octadecylglycero-3-phosphocholine,
2-O-ethylcarbamoyl-1-O-octadecylglycero-3-phosphocholine,
1-O-octadecyl-2-O-propylcarbamoylglycero-3-phosphocholine,
2-O-isopropylcarbamoyl-1-O-octadecylglycero-3-phosphocholine,
2-O-butylcarbamoyl-1-O-octadecylglycero-3-phosphocholine,
1-O-octadecyl-2-O-pentylcarbamoylglycero-3-phosphocholine and
2-O-hexylcarbamoyl-1-O-octadecylglycero-3-phosphocholine.

EXAMPLE 6

1-O-Hexadecyl-3-O-methylcarbamoylglycero-2-phosphocholine. A mixture of 50 mg of 1-O-hexadecylglycero-2-phosphocholine, 24 mg of methyl isocyanate, 5 ml of absolute chloroform and 0.1 ml of dimethylformamide is stirred at 40°–60° C. until the lysophospholipid can no longer be detected by thin-layer chromatography (Rf: 0.23). The solvent and excess methyl isocyanate are removed in vacuo and the residue is purified by column chromatography (silica gel/chloroform/methanol/water).

Yield: 45 mg, Rf: 0.26, IR: 1712 cm$^{-1}$.

The following are prepared analogously to these directions:

EXAMPLE 7

3-O-Ethylcarbamoyl-1-O-hexadecylglycero-2-phosphocholine from 50 mg of 1-O-hexadecylglycero-2-phosphocholine and 28 mg of ethyl isocyanate in 5 ml of chloroform and 0.1 ml of dimethylformamide.

Yield: 49 mg, Rf: 0.30, IR: 1715 cm$^{-1}$.

EXAMPLE 8

1-O-Hexadecyl-3-O-propylcarbamoylglycero-2-phosphocholine from 50 mg of 1-O-hexadecylglycero-2-phosphocholine and 34 mg of propyl isocyanate in 5 ml of chloroform and 0.1 ml of dimethylformamide.

Yield: 40 mg, Rf: 0.33, IR: 1710 cm$^{-1}$.

EXAMPLE 9

1-O-Hexadecyl-3-O-isopropylcarbamoylglycero-2-phosphocholine from 50 mg of 1-O-hexadecylglycero-2-phosphocholine and 34 mg of isopropyl isocyanate in 5 ml of chloroform and 0.1 ml of dimethylformamide.

Yield: 30 mg, Rf: 0.34, IR: 1715 cm$^{-1}$.

EXAMPLE 10

3-O-Butylcarbamoyl-1-O-hexadecylglycero-2-phosphocholine from 50 mg of 1-O-hexadecylglycero-2-phosphocholine and 40 mg of butyl isocyanate in 5 ml of chloroform and 0.1 ml of dimethylformamide.

Yield: 35 mg, Rf: 0.37, IR: 1710 cm$^{-1}$.

EXAMPLE 11

3-O-Methylcarbamoyl-1-O-octadecylglycero-2-phosphocholine from 50 mg of 1-O-octadecylglycero-2-phosphocholine and 24 mg of methyl isocyanate in 5 ml of chloroform and 0.1 ml of dimethylformamide.

Yield: 40 mg, Rf: 0.27, IR: 1715 cm$^{-1}$.

EXAMPLE 12

3-O-Ethylcarbamoyl-1-O-octadecylglycero-2-phosphocholine from 50 mg of 1-O-octadecylglycero-2-phosphocholine and 28 mg of ethyl isocyanate in 5 ml of chloroform and 0.1 ml of dimethylformamide.

Yield: 45 mg, Rf: 0.30, IR: 1712 cm$^{-1}$.

EXAMPLE 13

1-O-Octadecyl-3-O-propylcarbamoylglycero-2-phosphocholine from 50 mg of 1-O-octadecylglycero-2-phosphocholine and 34 mg of propyl isocyanate in 5 ml of chloroform and 0.1 ml of dimethylformamide.

Yield: 35 mg, Rf: 0.34, IR: 1715 cm$^{-1}$.

EXAMPLE 14

3-O-isopropylcarbamoyl-1-O-octadecylglycero-2-phosphocholine from 50 mg of 1-O-octadecylglycero-2-phosphocholine and 34 mg of isopropyl isocyanate in 5 ml of chloroform and 0.1 ml of dimethylformamide.

Yield: 32 mg, Rf: 0.34, IR: 1715 cm$^{-1}$.

EXAMPLE 15

3-O-Butylcarbamoyl-3-O-octadecylglycero-2-phosphocholine from 50 mg of 1-O-octadecylglycero-2-phosphocholine and 40 mg of butyl isocyanate in 5 ml of chloroform and 0.1 ml of dimethylformamide.

Yield: 38 mg, Rf: 0.38, IR: 1712 cm$^{-1}$.

EXAMPLE 16

3-O-Dimethylcarbamoyl-1-O-octadecylglycero-2-phosphocholine.

A mixture of 50 mg of 1-O-octadecylglycero-2-phosphocholine, 20 ml of dimethylcarbamoyl chloride and 55 mg of silver carbonate in 5 ml of chloroform is stirred for 24 hours at 50° C., the solvent is removed in vacuo and the residue is purified by column chromatography (silica gel: chloroform/methanol/water).

Yield: 35 mg, Rf: 0.47.

The following is prepared analogously to these directions:

EXAMPLE 17

3-O-Dimethylcarbamoyl-1-O-hexadecylglycero-2-phosphocholine from 50 mg of 1-O-hexadecylglycero-2-phosphocholine, 21 mg of dimethylcarbamoyl chloride and 55 mg of Ag$_2$CO$_3$ in 5 ml of chloroform.

Yield: 40 mg, Rf: 0.46.

The following are prepared analogously to

EXAMPLES 6–15

1-O-hexadecyl-3-O-pentylcarbamoylglycero-2-phosphocholine,
1-O-hexadecyl-3-O-hexylcarbamoylglycero-2-phosphocholine,
1-O-octadecyl-3-O-pentylcarbamoylglycero-2-phosphocholine,
3-O-hexylcarbamoyl-1-O-octadecylglycero-2-phosphocholine,
1-O-linolyl-3-O-methylcarbamoylglycero-2-phosphocholine,
3-O-ethylcarbamoyl-1-O-linolylglycero-2-phosphocholine,
1-O-linolyl-3-O-propylcarbamoylglycero-2-phosphocholine,
3-O-butylcarbamoyl-1-O-linolylglycero-2-phosphocholine,
1-O-linolyl-3-O-pentylcarbamoylglycero-2-phosphocholine,
3-O-hexylcarbamoyl-1-O-linolylglycero-2-phosphocholine,
3-O-methylcarbamoyl-1-O-oleylglycero-2-phosphocholine,
3-O-ethylcarbamoyl-1-O-oleylglycero-2-phosphocholine,
1-O-oleyl-3-O-propylcarbamoylglycero-2-phosphocholine,
3-O-butylcarbamoyl-1-O-oleylglycero-2-phosphocholine,
1-O-oleyl-3-O-pentylcarbamoylglycero-2-phosphocholine and
3-O-hexylcarbamoyl-1-O-oleylglycero-2-phosphocholine.

EXAMPLE 18

1-O-Hexadecyl-2-O-hexadecylcarbamoylglycero-3-phosphocholine.

A mixture of 50 mg of 1-O-hexadecylglycero-3-phosphocholine, 107 mg of hexadecyl isocyanate, 5 ml of chloroform and 0.1 ml of dimethylformamide is stirred at 60° C. for 48 hours. The excess alkyl isocyanate is hydrolysed by adding a little water and the mixture is concentrated in vacuo to a large extent. The residue is purified by preparative thin-layer chromatography (silica gel: chloroform/methanol/water=65/25/4).

Yield: 45 mg, Rf: 0.5, IR: 1710 cm$^{-1}$.

The following are prepared analogously:
1-O-hexadecyl-2-O-octadecylcarbamoylglycero-3-phosphocholine,
2-O-hexadecylcarbamoyl-1-O-octadecylglycero-3-phosphocholine,
1-O-octadecyl-2-O-octadecylcarbamoylglycero-3-phosphocholine,
2-O-decylcarbamoyl-1-O-hexadecylglycero-3-phosphocholine,
1-O-hexadecyl-2-O-undecylcarbamoylglycero-3-phosphocholine,
2-O-dodecylcarbamoyl-1-O-hexadecylglycero-3-phosphocholine,
1-O-hexadecyl-2-O-tetradecylcarbamoylglycero-3-phosphocholine,
2-O-eicosylcarbamoyl-1-O-hexadecylglycero-3-phosphocholine,
2-O-decylcarbamoyl-1-O-octadecylglycero-3-phosphocholine,
1-O-octadecyl-2-O-undecylcarbamoylglycero-3-phosphocholine,
2-O-dodecylcarbamoyl-1-O-octadecylglycero-3-phosphocholine,
1-O-octadecyl-2-O-tetradecylcarbamoylglycero-3-phosphocholine and
2-O-eicosylcarbamoyl-1-O-octadecylglycero-3-phosphocholine.

EXAMPLE 19

1-O-Hexadecyl-3-O-hexadecylcarbamoylglycero-2-phosphocholine.

A mixture of 50 mg of 1-O-hexadecylglycero-2-phosphocholine, 107 mg of hexadecyl isocyanate, 5 ml of chloroform and 0.1 ml of dimethylformamide is stirred at 60° C. for 48 hours. The excess alkyl isocyanate is hydrolysed by adding a little water and the mixture is concentrated in vacuo to a large extent. The residue is purified by preparative thin-layer chromatography (silica gel: chloroform/methanol/water=65/25/4).

Yield: 52 mg, Rf: 0.5, IR: 1712 cm$^{-1}$.

The following are prepared analogously to these directions:

EXAMPLE 20

1-O-Hexadecyl-3-O-octadecylcarbamoylglycero-2-phosphocholine from 50 mg of 1-O-hexadecylglycero-2-phosphocholine and 120 mg of octadecyl isocyanate in 5 ml of chloroform and 0.1 ml of dimethylformamide.

Yield: 61 mg, Rf: 0.5, IR: 1715 cm$^{-1}$.

EXAMPLE 21

3-O-Hexadecylcarbamoyl-1-O-octadecylglycero-2-phosphocholine from 50 mg of 1-O-octadecylglycero-2-phosphocholine and 100 mg of hexadecyl isocyanate in 5 ml of chloroform and 0.1 ml of dimethylformamide.

Yield: 48 mg, Rf: 0.51, IR: 1710 cm$^{-1}$.

EXAMPLE 22

1-O-Octadecyl-3-O-octadecylcarbamoylglycero-2-phosphocholine from 50 mg of 1-O-octadecylglycero-2-phosphocholine and 120 mg of octadecyl isocyanate in 5 ml of chloroform and 0.1 ml of dimethylformamide.

Yield: 54 mg, Rf: 0.52, IR: 1712 cm$^{-1}$.

The following are prepared analogously to Examples 19–22:

3-O-decylcarbamoyl-1-O-hexadecylglycero-2-phosphocholine,
1-O-hexadecyl-3-O-undecylcarbamoylglycero-2-phosphocholine,
3-O-dodecylcarbamoyl-1-O-hexadecylglycero-2-phosphocholine,
1-O-hexadecyl-3-O-tetradecylcarbamoylglycero-2-phosphocholine,
3-O-eicosylcarbamoyl-1-O-hexadecylglycero-2-phosphocholine,
1-O-decylcarbamoyl-3-O-octadecylglycero-2-phosphocholine,
1-O-octadecyl-3-O-undecylcarbamoylglycero-2-phosphocholine,
3-O-dodecylcarbamoyl-1-O-octadecylglycero-2-phosphocholine,
1-O-octadecyl-3-O-tetradecylcarbamoylglycero-2-phosphocholine,
3-O-eicosylcarbamoyl-1-O-octadecylglycero-2-phosphocholine,
3-O-hexadecylcarbamoyl-1-O-oleylglycero-2-phosphocholine and
3-O-hexadecylcarbamoyl-1-O-linoleyl-2-phosphocholine.

What we claim is:

1. O-Alkyl-O-carbamoylglycerophosphocholines of the general formulae I or II

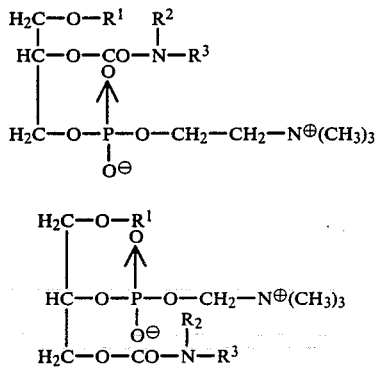

wherein $R^1$ denotes a straight-chain, saturated or unsaturated hydrocarbon radical having 10–20 C atoms, and $R^2$ and $R^3$ can be identical or different and denote a straight-chain or branched, saturated or unsaturated hydrocarbon radical having 1–20 C atoms, or a hydrogen atom, provided that at least one of $R^2$ and $R^3$ is a hydrocarbon radical as defined herein.

2. 1-O-Alkyl-2-O-carbamoylglycero-3-phosphocholines of the general formula I wherein $R^1$ denotes a straight-chain, saturated hydrocarbon radical having 10–20 C atoms, $R^2$ denotes a hydrogen atom and $R^3$ denotes a straight-chain or branched hydrocarbon radical having 1–9 C atoms.

3. 1-O-Alkyl-2-O-carbamoylglycero-3-phosphocholines according to claim 2, characterised in that $R^1$ is a straight-chain, saturated hydrocarbon radical having 16, 18 or 20 C atoms while $R^2$ denotes a hydrogen atom and $R^3$ denotes a methyl, ethyl or isopropyl radical.

4. 1-O-Alkyl-3-O-carbamoylglycero-2-phosphocholines of the general formula II wherein $R^1$ is a straight-chain, saturated or unsaturated hydrocarbon radical having 10–20 C atoms, while $R^2$ and $R^3$ can be identical or different and denote a straight-chain or branched hydrocarbon radical having 1–6 C atoms, or a hydrogen atom, provided that at least one of $R^2$ and $R^3$ is a hydrocarbon radical as defined herein.

5. 1-O-Alkyl-3-O-carbamoylglycero-2-phosphocholines according to claim 4, characterised in that $R^1$ is a straight-chain, saturated hydrocarbon radical having 16, 18 or 20 C atoms, while $R^2$ and $R^3$ can be identical or different and denote a straight-chain or branched hydrocarbon radical having 1–3 C atoms, or a hydrogen atom.

6. 1-O-Alkyl-3-O-carbamoylglycero-2-phosphocholines according to claim 4, characterised in that $R^1$ is a straight-chain hydrocarbon radical which has monoolefinic or diolefinic unsaturation and has 16, 18 or 20 C atoms, while $R^2$ and $R^3$ can be identical or different and denote a straight-chain or branched hydrocarbon radical having 1–3 C atoms, or a hydrogen atom.

7. 1-O-Alkyl-2-O-carbamoylglycero-3-phosphocholines of the general formula I wherein $R^1$ denotes a straight-chain, saturated hydrocarbon radical having 10–20 C atoms, $R^2$ denotes a hydrogen atom and $R^3$ denotes a straight-chain, saturated hydrocarbon radical having 10–20 C atoms, it being possible for $R^1$ and $R^3$ to be identical or different.

8. 1-O-Alkyl-2-O-carbamoylglycero-3-phosphocholines according to claim 7, characterised in that $R^1$ and $R^3$ denote a straight-chain, saturated hydrocarbon radical having 16 or 18 C atoms, it being possible for $R^1$ and $R^3$ to be identical or different.

9. 1-O-Alkyl-3-O-carbamoylglycero-2-phosphocholines of the general formula II wherein $R^1$ is a straight-chain, saturated or unsaturated hydrocarbon radical having 10–20 C atoms, $R^2$ denotes a hydrogen atom and $R^3$ denotes a straight-chain, saturated or unsaturated hydrocarbon radical having 10–20 C atoms, it being possible for $R^1$ and $R^3$ to be identical or different.

10. 1-O-Alkyl-3-O-carbamoylglycero-2-phosphocholines according to claim 9, characterised in that $R^1$ and $R^3$ denote a straight-chain, saturated or unsaturated hydrocarbon radical having 16 or 18 C atoms, it being possible for $R^1$ and $R^3$ to be identical or different.

11. Process for the treatment of human beings suffering from hypertension wherein a compound according to one of claims 1 to 10 are administered to the human beings so suffering.

* * * * *

UNITED STATES PATENT AND TRADEMARK OFFICE
CERTIFICATE OF CORRECTION

PATENT NO. : 4,552,869
DATED : November 12, 1985
INVENTOR(S) : Hans-Heiner Lautenschlager et al.

It is certified that error appears in the above-identified patent and that said Letters Patent are hereby corrected as shown below:

On the cover page, Section [56] References Cited, the first reference under "Other Publications" should read:

-- Breithaupt, "Med. Welt," vol. 33, (1982), p.1141 A.--;

Column 3, last line, after "techniques" insert --(for example German Offenlegungsschrift 2,712,031);

Column 8, last line, after "analogously to" insert --examples 6-15:--;

Column 9, first line, delete "EXAMPLES 6-15"; and

Claim 1, formula II should be changed to the following:

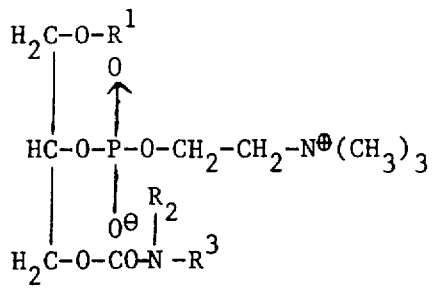

Signed and Sealed this

Twenty-second Day of July 1986

[SEAL]

Attest:

DONALD J. QUIGG

Attesting Officer        Commissioner of Patents and Trademarks